United States Patent [19]

Swimmer et al.

[11] Patent Number: 5,824,775
[45] Date of Patent: Oct. 20, 1998

[54] HUMAN NETRIN-1

[75] Inventors: Candace Swimmer, Winchester; Anne Shyjan, Nahant, both of Mass.; David Leonardo; Yuan Zhang, both of San Franscisco, Calif.; Timothy Kennedy, Montreal, Canada; Tito Serafini, San Francisco; Marc Tessier-Lavigne, San Mateo, both of Calif.

[73] Assignee: The Regents of the University of California, Oakland, Calif.

[21] Appl. No.: 635,137

[22] Filed: Apr. 19, 1996

[51] Int. Cl.[6] .............................. C07K 1/00; C07K 14/00; C07K 17/00

[52] U.S. Cl. ................................ 530/350; 530/397; 514/2

[58] Field of Search ...................................... 530/350, 399; 514/2

[56] References Cited

U.S. PATENT DOCUMENTS 5,565,331   10/1996   Tessier-Lavigne et al. .

*Primary Examiner*—Paula K. Hutzell
*Assistant Examiner*—Heather A. Bakalyar
*Attorney, Agent, or Firm*—Richard Aron Osman

[57] ABSTRACT

Specific netrin proteins, nucleic acids which encode netrin proteins and hybridization reagents, probes and primers capable of hybridizing with netrin genes and methods for screening chemical libraries for lead compounds for pharmacological agents useful in the diagnosis or treatment of disease associated undesirable cell growth are provided. An exemplary screen involves forming a mixture comprising a recombinant netrin protein, a natural intracellular netrin protein binding target, and a candidate pharmacological agent; incubating the mixture under conditions whereby, but for the presence of said candidate pharmacological agent, said netrin protein selectively binds said binding target; and detecting the presence or absence of specific binding of said netrin protein to said binding target.

1 Claim, No Drawings

HUMAN NETRIN-1

INTRODUCTION

1. Field of the Invention

The field of this invention is human netrin proteins and genes.

2. Background

In the developing nervous system, axons project considerable distances along stereotyped pathways to reach their targets. Axon growth and guidance depends partly on the recognition of cell-surface and extracellular matrix cues along these pathways. The identification of such nerve cell growth and guidance cues is the holy grail of neurobiology. These are the compounds that tell neurons when to grow, where to grow, and when to stop growing. The medical applications of such compounds are enormous and include modulating neuronal growth regenerative capacity, treating neurodegenerative disease, and mapping (e.g. diagnosing) genetic neurological defects.

Over decades of concentrated research, various hypotheses involving chemo-attractants and repellents, labeled pathways, cell adhesion molecules, etc. have been invoked to explain guidance. Molecules such as N-CAM and N-cadherin have been reported to provide favorable substrates for axon growth and certain sensory axons may be responsive to NGF and NGF-like factors. Recent reports suggest the existence of diffusible chemotropic molecule(s) which influence the pattern and orientation of commissural axon growth.

RELEVANT LITERATURE

Ishii et al. (1992) Neuron 9, 873–881 disclose a gene, unc-6, derived from C. elegans, which has sequence similarity to the disclosed netrins. Serafini et al (1994) Cell 78, 409–424 and Kennedy et al (1994) Cell 78, 425–435 at page 5, column 1 describe related vertebrate netrins. The work was also reported in *The New York Times,* Section B7, Tuesday, Aug. 16, 1994 and more recently (May 19, 1995) described in Science 268, 971–973 (see also references cited therein).

SUMMARY OF THE INVENTION

The invention provides methods and compositions relating to a human netrin protein and gene. Netrins are a class of proteins which are naturally involved in neural axon guidance. The subject compositions include nucleic acids which encode the specified netrin protein and hybridization probes and primers capable of hybridizing with the specified netrin gene. The netrin proteins finds particular use in modulating neural axon outgrowth. The disclosed compositions also find use variously in screening chemical libraries for regulators of axon outgrowth and orientation, in genetic mapping, as probes for netrin genes, as diagnostic reagents for genetic neurological disease and in the production of specific cellular and animal systems for the development of neurological disease therapy.

DETAILED DESCRIPTION OF THE INVENTION

The invention provides methods and compositions relating to a human netrin-1 protein and gene; including methods and compositions for identifying, purifying, characterizing, and producing the subject proteins and for identifying, characterizing, cloning, expressing, inhibiting the expression of and amplifying the subject nucleic acids. The subject proteins may be incomplete translates of the disclosed netrin cDNA sequence or deletion mutants of the corresponding conceptual translates, which translates or deletion mutants have the human netrin-1 binding activity and specificity described herein. The netrins are isolated, partially pure or pure and are typically recombinantly produced. An "isolated" protein for example, is unaccompanied by at least some of the material with which it is associated in its natural state; generally constituting at least about 0.5%, preferably at least about 2%, and more preferably at least about 10% by weight of the total protein in a given sample; and a pure protein constitutes at least about 50%, preferably at least about 90%, and more preferably at least about 99% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The disclosed netrin compositions may be used to modulate axon outgrowth or guidance in situ or in vivo. For in vivo applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Netrins may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, embedding or derivatizing fibers, such as collagen fibers, protein polymers, etc. with therapeutic proteins. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 $\mu$g/kg of the recipient and the concentration will generally be in the range of about 50 to 500 $\mu$g/ml in the dose administered. Other additives may be included, such as stabilizers, bactericides, etc. will be present in conventional amounts.

The invention provides netrin-specific binding agents including isolated binding targets such as membrane-bound netrin receptors and netrin-specific antibodies and binding agents identified in screens of natural and synthetic chemical libraries, and methods of identifying and making such agents, and their use in diagnosis, therapy and pharmaceutical development. Generally, netrin-specificity of the binding agent is shown by binding equilibrium constants. Such agents are capable of selectively binding the specified netrin, i.e. with an equilibrium constant at least about $10^7 M^{-1}$, preferably at least about $10^8 M^{-1}$, more preferably at least about $10^9 M^{-1}$. A wide variety of cell-based and cell-free assays may be used to demonstrate netrin-specific binding; preferred are rapid in vitro, cell-free assays such as mediating or inhibiting netrin-cell/protein binding, immunoassays, etc.

The invention also provides nucleic acids encoding the subject proteins, which nucleic acids may be part of netrin-expression vectors and may be incorporated into recombinant cells for expression and screening, transgenic animals for functional studies (e.g. the efficacy of candidate drugs for neural disease or injury), etc. and nucleic acid hybridization probes and replication/amplification primers having a disclosed netrin cDNA specific sequence. The hybridization probes contain a sequence common or complementary to the corresponding netrin gene sufficient to make the probe capable of specifically hybridizing to the corresponding netrin gene, and only to the corresponding netrin gene, in the presence of other netrin genes. Hence, the subject probes and primers are uniquely specific to the disclosed cDNA. Hybridization probes having in excess of 100 continuous bases of netrin gene sequence are generally capable of hybridizing to the corresponding netrin cDNA and remaining bound at a reduced final wash stringency of 0.2×SSC (0.9 M saline/0.09 M sodium citrate) and 0.1% SDS buffer at a temperature of 65° C.

The subject nucleic acids are isolated, meaning they comprise a sequence joined to a nucleotide other than that which it is joined to on a natural chromosome, and usually constitute at least about 0.5%, preferably at least about 2%, and more preferably at least about 5% by weight of total nucleic acid present in a given fraction. A pure nucleic acid constitutes at least about 50%, preferably at least about 90%, and more preferably at least about 95% by weight of total nucleic acid present in a given fraction. The subject nucleic acids find a wide variety of applications including use as translatable transcripts, hybridization probes, PCR primers, therapeutic nucleic acids, etc.; use in detecting the presence of netrin genes and gene transcripts, e.g. allele-specific oligonucleotide (ASO) probes use to identify wild-type and mutant netrin alleles in clinical and laboratory samples, in detecting or amplifying nucleic acids encoding other netrins, and in gene therapy applications, e.g. antisense oligonucleotides capable of inhibiting the intracellular expression of a targeted netrin transcript.

The invention provides efficient methods of identifying pharmacological agents or lead compounds for agents capable of mimicking or modulating netrin function (e.g. bioactive netrin deletion mutants and netrin peptides). A wide variety of screens may be used; for example, cell-based assays may be used for monitoring netrin function and in vitro binding assays may be used to identify netrin-specific binding agents. Kennedy et al. (1994) Cell 78, 425–435 describe a particularly convenient COS cell-based netrin expression assay. Preferred methods are amenable to automated, cost-effective high throughput screening of natural and synthetic chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

EXAMPLES

Human Netrin 1 (SEQ ID NO:2) and cDNA (SEQ ID NO:1).

We isolated chicken netrin 1 and 2 cDNAs as described in Serafini et al. (1974) Cell 78:409–424. Based on the chick netrin 1 and 2 cDNA sequences, we designed degenerate oligonucleotide primers and used these primers to amplify a cDNA encoding mouse netrin 1 from a murine cDNA library. We then isolated a human netrin cDNA using degenerate oligonucleotide primers constructed using amino acid sequences conserved in chick and mouse netrin sequences as a guide.

The starting material for PCR was 100 ng of human genomic DNA. Two rounds of PCR amplification were used. In the first round, the following program and conditions were used: 1. 94° C. 30 sec.; 2. 50° C. 45 sec; 3. 72° C., 1 minute; 4. go to 1, 30 times; 5. 4° C.; 6. end. In the second round of PCR amplification, nested PCR and the following conditions and program were used: 1. 94° C. 1 minute; 2. 42° C. 1 minute; 3. increments of 1° C. every 5 seconds to 72° C.; 4. 72° C. for 3 minutes; 5. go to 1, 2 times; 6. 94° C. for 1 minute; 7. 46° C. for 1 minute; 8. increments of 1° C. every 6 seconds until 72° C.; 9. 72° C. 2 minutes; 10. go to 6, 7 times; 11. 94° C. for 1 minute; 12. 55° C. for 1 minute; 13. 72° C. 2 minute; 14. go to 11, 24 times; 15. 94° C. for 1 minute; 16. 55° C. for 1 minute; 17. 72° C. for 10 minutes; 18. 4° C.; 19. end. PCR products were subcloned and individual clones containing inserts corresponding to human netrin sequence isolated using a Grunstein and Hogness screen (Sambrook, 1989). $^{32}$P was incorporated into a probe using PCR with a portion of the mouse netrin-1 cDNA clone as a template. The final wash of the filters was at a reduced stringency of 1× SSC and 0.1% SDS at 65° C. (Sambrook et al., 1989). This screen isolated an approximately 140 base pair human netrin CDNA clone. This cDNA fragment was used to isolate a longer human netrin cDNA from a Human fetal brain cDNA library (Stratagene cat#936206). The ~140 base pair human netrin cDNA was used as a template and $^{32}$P incorporated into a human netrin cDNA probe using PCR. 1×10$^6$ clones were screened at high stringency (Sambrook et al., 1989) identifying a single approximately 7 kb netrin cDNA (HBC-1, deposited with ATCC Jun. 7, 1995, as plasmid HN-1, deposit number 97204).

Sequence analysis determined that an EcoRI subclone of the 7 kb HBC-1 clone corresponded to a splice variant of human netrin-1. The first 1086 base pairs of sequence show high homology to mouse netrin-1 and the remaining 626 base pairs are highly divergent. A potential splice donor site is identified at the junction of the netrin and the divergent sequence. A clone that corresponds to the 3' end of human netrin-1 was isolated using reverse transcription and PCR with a 5' primer at position 999 of the human sequence and a 3' degenerate primer to the last 15 base pairs of the mouse netrin sequence. Three additional independent clones were isolated to confirm the sequence of the PCR reaction product. The region of overlap between this new clone and the HBC-1 Eco clone is 46 base pairs and is identical in sequence. To verify the overlap, an additional clone was isolated using a 5' primer at position 818 and a 3' primer at position 1582 of the human netrin-1 sequence. Two independent clones isolated using these primers confirm the structure of the cDNA. Finally, the sequence encoding the C-terminal 5 amino acids was confirmed. A primer was designed to a region within the 3' untranslated region that is conserved between chicken and mouse netrin-1. A PCR product was generated using this primer and a 5' primer in the human sequence at position 1568 and the sequence was verified.

RT-PCR procedures were as follows: fetal brain RNA (19–23 weeks) was obtained from Clontech. RT-PCR was performed using the GeneAmp Thermostable rTth Reverse Transcriptase RNA PCR Kit from Perkin Elmer. A hot start technique was used to denature the RNA by mixing 50 ng with 30 pmol degenerate primer deg-1, 1 $\mu$l 10× rTth Reverse Transcriptase Buffer (Perkin Elmer) and water in a total volume of 7.2 $\mu$l; this mixture was heated to 95° C. for 2 minutes, followed by a 5 minute incubation at 70° C. The reaction was cooled to 60° C. and reverse transcription was begun by adding a mixture containing 1 $\mu$l 10 mM MnCl$_2$, 1 $\mu$l rTth DNA polymerase (Perkin Elmer, 2.5 U), and 0.2 $\mu$l each 10 mM dATP, dCTP, dGTP, and dTTP. The 60° C.

incubation was continued for 5 minutes, followed by two 5 minute incubations at 65° C. and 70° C. The reaction was then chilled on ice.

To amplify the human netrin-1 fragment by PCR, a mixture containing 2 μl DMSO, 3 μl 25 mM MgCl$_2$, 4 μl 10× Chelating Buffer (Perkin Elmer) and 34.5 μl water was added to the reverse transcription reaction. 30 pmol of a human netrin-specific primer, h-net-5'999, was added (0.5 μl) to the mixture and PCR was carried out in an MJ Research PTC-200 Peltier Thermal Cycler using the "Calculated" temperature control method and the following conditions: 1) 95° C. for 2 minutes; 2) 55° C. for 25 seconds; 3) 95° C. for 10 seconds; 4) Repeat steps 2–3, 34 times; 5) 60° C. for 7 minutes; and 6) 4° C. hold.

The reaction was analyzed by gel electrophoresis and transferred to nylon membrane. Netrin-specific products were detected by Southern hybridization using a mouse netrin probe corresponding to sequence from position 1342 to position 1875 of mouse netrin. A plug of agarose corresponding to the cross hybridizing fragment (migrating at approximately 850 bp) was extracted with a Pasteur pipet and reamplified as follows: the agarose plug was combined with a reaction mixture containing 1.25 μl formamide, 5 μl of 10× PCR Buffer II (Perkin Elmer), 5 μl of 25 mM MgCl$_2$, 30 pmol human netrin-specific primer h-net-5'999, 30 pmol degenerate netrin primer deg-1, 5 U AmpliTaq DNA Polymerase (Perkin Elmer), and sterile water in a total volume of 49 μl. PCR was carried out in an MJ Research PTC-200 Peltier Thermal Cycler using the "Block" temperature control method and the following conditions: 1) 95° C. for 2 minutes; 2) 50° C. for 1 minute; 3) 75° C. for 1 minute, 30 seconds; 4) 95° C. for 20 seconds; 5) Repeat steps 2–4, 39 times; 6) 75° C. for 10 minutes; and 7) 4° C. hold.

The reaction was analyzed by gel electrophoresis and a band of DNA at approximately 850 bp was purified using the BioRad Prep-A-Gene system, ligated with the TA cloning vector (InVitroGen), and transformed into DH5α competent bacterial cells. Colonies were analyzed for the correct size insert by colony PCR, grown overnight at 37° C. in LB media containing 100 μg/ml ampicillin, and DNA was prepared from the culture using a Qiagen Tip-100 column. The inserts were confirmed by restriction digests and the sequence was generated using an ABI 377 automated sequencer.

To confirm the last 15 nucleotides of the human netrin-1 clone, the 3' end of the clone was amplified from first strand cDNA using a 5' primer to known sequence and a 3' primer to sequence in the 3' untranslated region of the mouse netrin-1 clone. First, cDNA was synthesized as described in "Rapid Amplification of cDNA Ends," by Michael Frohman (In: PCR Primer: A Laboratory Manual, C. W. Dieffenbach and G. S. Dveksler, eds., Cold Spring Harbor Laboratory Press, 1995) using the protocol described in the section "3'-End cDNA Amplification" (pp. 388–389), and 1 μg fetal brain poly A+ RNA (Clontech). 1 μl of the diluted cDNA was amplified in a 50 μl reaction containing 67 mM Tris HCl, pH 9.0, 6.7 mM magnesium chloride, 16.6 mM ammonium sulfate, 0.17 mg/ml BSA, 10% DMSO, 1.5 mM each dNTP, 30 pmol 5'primer "h-net 5'1449" and 30 pmol 3' primer "m-net 3' UT 2238". The primer "h-net 5'1449" corresponds to sequence beginning at position 1449 in the human netrin-1 clone. The primer "m-net 3' UT 2238" corresponds to sequence in the 3' untranslated region of mouse netrin-1, with the addition of an Xba I restriction site sequence at the 5' end. Taq DNA polymerase, 1 μl, (Perkin Elmer) was combined with 0.5 μl TaqStart Antibody (ClonTech) and 2.5 μl TaqStart Antibody Dilution Buffer, incubated at room temperature for 10 minutes, and added to the PCR reaction mixture. The reaction was amplified in an MJ Research PTC-200 Peltier Thermal Cycler using the "Calculated" temperature control method and the following conditions: 1) 95° C. for 2 minutes; 2) 62° C. for 30 seconds; 3) 57° C. for 30 seconds; 4) 52° C. for 10 seconds; 5) 72° C. for 40 minutes; 6) 94° C. for 10 seconds; 7) 62° C. for 1 minute; 8) 72° C. for 3 minutes; 9) Repeat steps 6–8, 4 times; 10) 94° C. for 10 seconds; 11) 57° C. for 1 minute; 12) 72° C. for 3 minutes; 13) Repeat steps 10–12, 4 times; 14) 94° C. for 10 seconds; 15) 52° C. for 1 minute; 16) 72° C. for 3 minutes; 17) Repeat steps 14–16, 24 times; 18) 75° C. for 10 minutes; 19) 4° C. hold.

The reaction was diluted 1:20 in TE, and 1 μl was re-amplified in a 50 μl reaction containing 67 mM Tris HCl, pH 9.0, 6.7 mM magnesium chloride, 16.6 mM ammonium sulfate, 0.17 mg/ml BSA, 10% DMSO, 1.5 mM each dNTP, 30 pmol of the 5'primer "h-net 5'1702," 30 pmol of the 3'primer "m-net 3'UT 2238" and 0.25 ul Taq DNA Polymerase. The primer "m-net 5'1702" corresponds to sequence beginning at position 1568 in the human netrin-1 clone. The reaction was amplified in an MJ Research PTC-200 Peltier Thermal Cycler using the "Calculated" temperature control method and the following conditions: 1) 95° C. for 2 minutes; 2) 94° C. for 10 seconds; 3) 58° C. for 1 minute; 4) 72° C. for 3 minutes; 5) Repeat steps 2–4, 4 times; 6) 94° C. for 10 seconds; 7) 54° C. for 45 seconds; 8) 72° C. for 3 minutes; 9) Repeat steps 6–8, 4 times; 10) 94° C. for 10 seconds; 11) 50° C. for 30 seconds; 12) 72° C. for 3 minutes; 13) Repeat steps 10–12, 24 times; 14) 75° C. for 5 minutes; and 15) 4° C. hold.

The reaction was analyzed by gel electrophoresis and a 530 bp product was isolated from the gel using the Prep-A-Gene System (BioRad). The product was ligated into pCR 2.1 (InVitroGen) overnight at 14° C. Transformants were cultured overnight in LB media containing 100 μg/ml ampicillin and DNA was purified from cultures using Easy Pure Plasmid Preps (Super Mini, Primm Labs). DNA sequence was generated using an ABI 377 automated sequencer.

To confirm the 3' end sequence, two additional fragments spanning the 3' end of human netrin were generated by PCR using the m-net 5'1702 primer and a 3' primer, h-net 3'1959 corresponding to sequence in the 3' untranslated region of human netrin-1. Amplification with these primers generated products of approximately 390 base pairs in duplicate reactions. The fragments were amplified in an MJ Research PTC-200 Peltier Thermal Cycler using the "Calculated" temperature control method and the following conditions: 1) 95° C. for 2 minutes; 2) 94° C. for 10 seconds; 3) 58° C. for 1 minute; 4) 72° C. for 3 minutes; 5) Repeat steps 2–4, 4 times; 6) 94° C. for 10 seconds; 7) 54° C. for 45 seconds; 8) 72° C. for 3 minutes; 9) Repeat steps 6–8, 4 times; 10) 94° C. for 10 seconds; 11) 50° C. for 30 seconds; 12) 72° C. for 3 minutes; 13) Repeat steps 10–12, 19 times; 14) 75° C. for 5 minutes; and 15) 4° C. hold. The reactions were analyzed by gel electrophoresis to confirm their size, and directly sequenced using an ABI 377 automated sequencer.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated netrin comprising the amino acid sequence of SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1848 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 34..1845

( x i ) SEQUENCE DESCRIPTION: SEQ ID NO:1:

```
GGCGCGGCAG GGCCGGGGCA AGCTGGACGC AGC ATG ATG CGC GCA GTG TGG GAG         54
                                    Met Met Arg Ala Val Trp Glu
                                    1               5

GCG CTG GCG GCG CTG GCG GCG GTG GCG TGC CTG GTG GGC GCG GTG CGC        102
Ala Leu Ala Ala Leu Ala Ala Val Ala Cys Leu Val Gly Ala Val Arg
            10                  15                  20

GGC GGG CCC GGG CTC AGC ATG TTC GCG GGC CAG GCG GCG CAG CCC GAT        150
Gly Gly Pro Gly Leu Ser Met Phe Ala Gly Gln Ala Ala Gln Pro Asp
        25                  30                  35

CCC TGC TCG GAC GAG AAC GGC CAC CCG CGC CGC TGC ATC CCG GAC TTT        198
Pro Cys Ser Asp Glu Asn Gly His Pro Arg Arg Cys Ile Pro Asp Phe
40                  45                  50                  55

GTC AAT GCG GCC TTC GGC AAG GAC GTG CGC GTG TCC AGC ACC TGC GGC        246
Val Asn Ala Ala Phe Gly Lys Asp Val Arg Val Ser Ser Thr Cys Gly
                60                  65                  70

CGG CCC CCG GCG CGC TAC TGC GTG GTG AGC GAG CGC GGC GAG GAG CGG        294
Arg Pro Pro Ala Arg Tyr Cys Val Val Ser Glu Arg Gly Glu Glu Arg
            75                  80                  85

CTG CGC TCG TGC CAC CTC TGC AAC GCG TCC GAC CCC AAG AAG GCG CAC        342
Leu Arg Ser Cys His Leu Cys Asn Ala Ser Asp Pro Lys Lys Ala His
        90                  95                  100

CCG CCC GCC TTC CTC ACC GAC CTC AAC AAC CCG CAC AAC CTG ACG TGC        390
Pro Pro Ala Phe Leu Thr Asp Leu Asn Asn Pro His Asn Leu Thr Cys
105                 110                 115

TGG CAG TCC GAG AAC TAC CTG CAG TTC CCG CAC AAC GTC ACG CTC ACA        438
Trp Gln Ser Glu Asn Tyr Leu Gln Phe Pro His Asn Val Thr Leu Thr
120                 125                 130                 135

CTG TCC CTC GGC AAG AAG TTC GAA GTG ACC TAC GTG AGC CTG CAG TTC        486
Leu Ser Leu Gly Lys Lys Phe Glu Val Thr Tyr Val Ser Leu Gln Phe
            140                 145                 150

TGC TCG CCG CGG CCC GAG TCC ATG GCC ATC TAC AAG TCC ATG GAC TAC        534
Cys Ser Pro Arg Pro Glu Ser Met Ala Ile Tyr Lys Ser Met Asp Tyr
        155                 160                 165

GGG CGC ACG TGG GTG CCC TTC CAG TTC TAC TCC ACG CAG TGC CGC AAG        582
Gly Arg Thr Trp Val Pro Phe Gln Phe Tyr Ser Thr Gln Cys Arg Lys
        170                 175                 180

ATG TAC AAC CGG CCG CAC CGC GCG CCC ATC ACC AAG CAG AAC GAG CAG        630
Met Tyr Asn Arg Pro His Arg Ala Pro Ile Thr Lys Gln Asn Glu Gln
        185                 190                 195

GAG GCC GTG TGC ACC GAC TCG CAC ACC GAC ATG CGC CCG CTC TCG GGC        678
Glu Ala Val Cys Thr Asp Ser His Thr Asp Met Arg Pro Leu Ser Gly
200                 205                 210                 215
```

| | | | | | | | | | | | | | | | | |
|---|---|---|---|---|---|---|---|---|---|---|---|---|---|---|---|---|
| GGC | CTC | ATC | GCC | TTC | AGC | ACG | CTG | GAC | GGG | CGG | CCC | TCG | GCG | CAC | GAC | 726 |
| Gly | Leu | Ile | Ala | Phe | Ser | Thr | Leu | Asp | Gly | Arg | Pro | Ser | Ala | His | Asp | |
| 220 | | | | 220 | | | | 225 | | | | | | 230 | | |

| | | | | | | | | | | | | | | | | |
|---|---|---|---|---|---|---|---|---|---|---|---|---|---|---|---|---|
| TTC | GAC | AAC | TCG | CCC | GTG | CTG | CAG | GAC | TGG | GTC | ACG | GCC | ACA | GAC | ATC | 774 |
| Phe | Asp | Asn | Ser | Pro | Val | Leu | Gln | Asp | Trp | Val | Thr | Ala | Thr | Asp | Ile | |
| | | | 235 | | | | 240 | | | | | 245 | | | | |

| | | | | | | | | | | | | | | | | |
|---|---|---|---|---|---|---|---|---|---|---|---|---|---|---|---|---|
| CGC | GTG | GCC | TTC | AGC | CGC | CTG | CAC | ACG | TTC | GGC | GAC | GAG | AAC | GAG | GAC | 822 |
| Arg | Val | Ala | Phe | Ser | Arg | Leu | His | Thr | Phe | Gly | Asp | Glu | Asn | Glu | Asp | |
| | | 250 | | | | | 255 | | | | | 260 | | | | |

| | | | | | | | | | | | | | | | | |
|---|---|---|---|---|---|---|---|---|---|---|---|---|---|---|---|---|
| GAC | TCG | GAG | CTG | GCG | CGC | GAC | TCG | TAC | TTC | TAC | GCG | GTG | TCC | GAC | CTG | 870 |
| Asp | Ser | Glu | Leu | Ala | Arg | Asp | Ser | Tyr | Phe | Tyr | Ala | Val | Ser | Asp | Leu | |
| | 265 | | | | | 270 | | | | | 275 | | | | | |

| | | | | | | | | | | | | | | | | |
|---|---|---|---|---|---|---|---|---|---|---|---|---|---|---|---|---|
| CAG | GTG | GGC | GGC | CGG | TGC | AAG | TGC | AAC | GGC | CAC | GCG | GCC | CGC | TGC | GTG | 918 |
| Gln | Val | Gly | Gly | Arg | Cys | Lys | Cys | Asn | Gly | His | Ala | Ala | Arg | Cys | Val | |
| 280 | | | | | 285 | | | | | 290 | | | | | 295 | |

| | | | | | | | | | | | | | | | | |
|---|---|---|---|---|---|---|---|---|---|---|---|---|---|---|---|---|
| CGC | GAC | CGC | GAC | GAC | AGC | CTG | GTG | TGC | GAC | TGC | AGG | CAC | AAC | ACG | GCC | 966 |
| Arg | Asp | Arg | Asp | Asp | Ser | Leu | Val | Cys | Asp | Cys | Arg | His | Asn | Thr | Ala | |
| | | | | 300 | | | | | 305 | | | | | 310 | | |

| | | | | | | | | | | | | | | | | |
|---|---|---|---|---|---|---|---|---|---|---|---|---|---|---|---|---|
| GGC | CCG | GAG | TGC | GAC | CGC | TGC | AAG | CCC | TTC | CAC | TAC | GAC | CGG | CCC | TGG | 1014 |
| Gly | Pro | Glu | Cys | Asp | Arg | Cys | Lys | Pro | Phe | His | Tyr | Asp | Arg | Pro | Trp | |
| | | | | 315 | | | | 320 | | | | | 325 | | | |

| | | | | | | | | | | | | | | | | |
|---|---|---|---|---|---|---|---|---|---|---|---|---|---|---|---|---|
| CAG | CGC | GCC | ACA | GCC | CGC | GAA | GCC | AAC | GAG | TGC | GTG | GCC | TGT | AAC | TGC | 1062 |
| Gln | Arg | Ala | Thr | Ala | Arg | Glu | Ala | Asn | Glu | Cys | Val | Ala | Cys | Asn | Cys | |
| | | 330 | | | | | 335 | | | | | 340 | | | | |

| | | | | | | | | | | | | | | | | |
|---|---|---|---|---|---|---|---|---|---|---|---|---|---|---|---|---|
| AAC | CTG | CAT | GCC | CGG | CGC | TGC | CGC | TTC | AAC | ATG | GAG | CTC | TAC | AAG | CTT | 1110 |
| Asn | Leu | His | Ala | Arg | Arg | Cys | Arg | Phe | Asn | Met | Glu | Leu | Tyr | Lys | Leu | |
| 345 | | | | | 350 | | | | | 355 | | | | | | |

| | | | | | | | | | | | | | | | | |
|---|---|---|---|---|---|---|---|---|---|---|---|---|---|---|---|---|
| TCG | GGG | CGC | AAG | AGC | GGA | GGT | GTC | TGC | CTC | AAC | TGT | CGC | CAC | AAC | ACC | 1158 |
| Ser | Gly | Arg | Lys | Ser | Gly | Gly | Val | Cys | Leu | Asn | Cys | Arg | His | Asn | Thr | |
| 360 | | | | | 365 | | | | | 370 | | | | | 375 | |

| | | | | | | | | | | | | | | | | |
|---|---|---|---|---|---|---|---|---|---|---|---|---|---|---|---|---|
| GCC | GGC | CGC | CAC | TGC | CAT | TAC | TGC | AAG | GAG | GGC | TAC | TAC | CGC | GAC | ATG | 1206 |
| Ala | Gly | Arg | His | Cys | His | Tyr | Cys | Lys | Glu | Gly | Tyr | Tyr | Arg | Asp | Met | |
| | | | | 380 | | | | | 385 | | | | | 390 | | |

| | | | | | | | | | | | | | | | | |
|---|---|---|---|---|---|---|---|---|---|---|---|---|---|---|---|---|
| GGC | AAG | CCC | ATC | ACC | CAC | CGG | AAG | GCC | TGC | AAA | GCC | TGT | GAT | TGC | CAC | 1254 |
| Gly | Lys | Pro | Ile | Thr | His | Arg | Lys | Ala | Cys | Lys | Ala | Cys | Asp | Cys | His | |
| | | | 395 | | | | 400 | | | | | 405 | | | | |

| | | | | | | | | | | | | | | | | |
|---|---|---|---|---|---|---|---|---|---|---|---|---|---|---|---|---|
| CCT | GTG | GGT | GCT | GCT | GGC | AAA | ACC | TGC | AAC | CAA | ACC | ACC | GGC | CAG | TGT | 1302 |
| Pro | Val | Gly | Ala | Ala | Gly | Lys | Thr | Cys | Asn | Gln | Thr | Thr | Gly | Gln | Cys | |
| | | 410 | | | | | 415 | | | | | 420 | | | | |

| | | | | | | | | | | | | | | | | |
|---|---|---|---|---|---|---|---|---|---|---|---|---|---|---|---|---|
| CCC | TGC | AAG | GAC | GGC | GTG | ACG | GGT | ATC | ACC | TGC | AAC | CGC | TGC | GCC | AAA | 1350 |
| Pro | Cys | Lys | Asp | Gly | Val | Thr | Gly | Ile | Thr | Cys | Asn | Arg | Cys | Ala | Lys | |
| | 425 | | | | | 430 | | | | | 435 | | | | | |

| | | | | | | | | | | | | | | | | |
|---|---|---|---|---|---|---|---|---|---|---|---|---|---|---|---|---|
| GGC | TAC | CAG | CAG | AGC | CGC | TCT | CCC | ATC | GCC | CCC | TGC | ATA | AAG | ATC | CCT | 1398 |
| Gly | Tyr | Gln | Gln | Ser | Arg | Ser | Pro | Ile | Ala | Pro | Cys | Ile | Lys | Ile | Pro | |
| 440 | | | | | 445 | | | | 450 | | | | | | 455 | |

| | | | | | | | | | | | | | | | | |
|---|---|---|---|---|---|---|---|---|---|---|---|---|---|---|---|---|
| GTA | GCG | CCG | CCG | ACG | ACT | GCA | GCC | AGC | AGC | GTG | GAG | GAG | CCT | GAA | GAC | 1446 |
| Val | Ala | Pro | Pro | Thr | Thr | Ala | Ala | Ser | Ser | Val | Glu | Glu | Pro | Glu | Asp | |
| | | | | 460 | | | | | 465 | | | | | 470 | | |

| | | | | | | | | | | | | | | | | |
|---|---|---|---|---|---|---|---|---|---|---|---|---|---|---|---|---|
| TGC | GAT | TCC | TAC | TGC | AAG | GCC | TCC | AAG | GGG | AAG | CTG | AAG | ATT | AAC | ATG | 1494 |
| Cys | Asp | Ser | Tyr | Cys | Lys | Ala | Ser | Lys | Gly | Lys | Leu | Lys | Ile | Asn | Met | |
| | | | 475 | | | | | 480 | | | | | 485 | | | |

| | | | | | | | | | | | | | | | | |
|---|---|---|---|---|---|---|---|---|---|---|---|---|---|---|---|---|
| AAA | AAG | TAC | TGC | AAG | AAG | GAC | TAT | GCC | GTC | CAG | ATC | CAC | ATC | CTG | AAG | 1542 |
| Lys | Lys | Tyr | Cys | Lys | Lys | Asp | Tyr | Ala | Val | Gln | Ile | His | Ile | Leu | Lys | |
| | | 490 | | | | | 495 | | | | | 500 | | | | |

| | | | | | | | | | | | | | | | | |
|---|---|---|---|---|---|---|---|---|---|---|---|---|---|---|---|---|
| GCG | GAC | AAG | GCG | GGG | GAC | TGG | TGG | AAG | TTC | ACG | GTG | AAC | ATC | ATC | TCC | 1590 |
| Ala | Asp | Lys | Ala | Gly | Asp | Trp | Trp | Lys | Phe | Thr | Val | Asn | Ile | Ile | Ser | |
| | | 505 | | | | | 510 | | | | | 515 | | | | |

| | | | | | | | | | | | | | | | | |
|---|---|---|---|---|---|---|---|---|---|---|---|---|---|---|---|---|
| GTG | TAT | AAG | CAG | GGC | ACG | AGC | CGC | ATC | CGC | CGC | GGT | GAC | CAG | AGC | CTG | 1638 |
| Val | Tyr | Lys | Gln | Gly | Thr | Ser | Arg | Ile | Arg | Arg | Gly | Asp | Gln | Ser | Leu | |
| 520 | | | | | 525 | | | | | 530 | | | | | 535 | |

| TGG | ATC | CGC | TCG | CGG | GAC | ATC | GCC | TGC | AAG | TGT | CCC | AAA | ATC | AAG | CCC | 1686 |
| Trp | Ile | Arg | Ser | Arg | Asp | Ile | Ala | Cys | Lys | Cys | Pro | Lys | Ile | Lys | Pro | |
| | | | | 540 | | | | 545 | | | | | 550 | | | |

| CTC | AAG | AAG | TAC | CTG | CTG | CTG | GGC | AAC | GCG | GAG | GAC | TCT | CCG | GAC | CAG | 1734 |
| Leu | Lys | Lys | Tyr | Leu | Leu | Leu | Gly | Asn | Ala | Glu | Asp | Ser | Pro | Asp | Gln | |
| | | | 555 | | | | 560 | | | | 565 | | | | | |

| AGC | GGC | ATC | GTG | GCC | GAT | AAA | AGC | AGC | CTG | GTG | ATC | CAG | TGG | CGG | GAC | 1782 |
| Ser | Gly | Ile | Val | Ala | Asp | Lys | Ser | Ser | Leu | Val | Ile | Gln | Trp | Arg | Asp | |
| | | 570 | | | | 575 | | | | | 580 | | | | | |

| ACG | TGG | GCG | CGG | CGG | CTG | CGC | AAG | TTC | CAG | CAG | CGT | GAG | AAG | AAG | GGC | 1830 |
| Thr | Trp | Ala | Arg | Arg | Leu | Arg | Lys | Phe | Gln | Gln | Arg | Glu | Lys | Lys | Gly | |
| | 585 | | | | 590 | | | | | 595 | | | | | | |

| AAG | TGC | AAG | AAG | GCC | TAG | | | | | | | | | | | 1848 |
| Lys | Cys | Lys | Lys | Ala | | | | | | | | | | | | |
| 600 | | | | | | | | | | | | | | | | |

(2) INFORMATION FOR SEQ ID NO:2:

(i) SEQUENCE CHARACTERISTICS:
        (A) LENGTH: 604 amino acids
        (B) TYPE: amino acid
        (D) TOPOLOGY: linear (ii) MOLECULE TYPE: protein (xi) SEQUENCE DESCRIPTION: SEQ ID NO:2:

| Met | Met | Arg | Ala | Val | Trp | Glu | Ala | Leu | Ala | Ala | Leu | Ala | Ala | Val | Ala |
| 1 | | | | 5 | | | | | 10 | | | | | 15 | |
| Cys | Leu | Val | Gly | Ala | Val | Arg | Gly | Gly | Pro | Gly | Leu | Ser | Met | Phe | Ala |
| | | | 20 | | | | | 25 | | | | | 30 | | |
| Gly | Gln | Ala | Ala | Gln | Pro | Asp | Pro | Cys | Ser | Asp | Glu | Asn | Gly | His | Pro |
| | | | 35 | | | | 40 | | | | | 45 | | | |
| Arg | Arg | Cys | Ile | Pro | Asp | Phe | Val | Asn | Ala | Ala | Phe | Gly | Lys | Asp | Val |
| | | 50 | | | | | 55 | | | | 60 | | | | |
| Arg | Val | Ser | Ser | Thr | Cys | Gly | Arg | Pro | Pro | Ala | Arg | Tyr | Cys | Val | Val |
| 65 | | | | | 70 | | | | | 75 | | | | | 80 |
| Ser | Glu | Arg | Gly | Glu | Glu | Arg | Leu | Arg | Ser | Cys | His | Leu | Cys | Asn | Ala |
| | | | | 85 | | | | | 90 | | | | | 95 | |
| Ser | Asp | Pro | Lys | Lys | Ala | His | Pro | Pro | Ala | Phe | Leu | Thr | Asp | Leu | Asn |
| | | | | 100 | | | | 105 | | | | | 110 | | |
| Asn | Pro | His | Asn | Leu | Thr | Cys | Trp | Gln | Ser | Glu | Asn | Tyr | Leu | Gln | Phe |
| | | | 115 | | | | 120 | | | | | 125 | | | |
| Pro | His | Asn | Val | Thr | Leu | Thr | Leu | Ser | Leu | Gly | Lys | Lys | Phe | Glu | Val |
| | | 130 | | | | 135 | | | | | 140 | | | | |
| Thr | Tyr | Val | Ser | Leu | Gln | Phe | Cys | Ser | Pro | Arg | Pro | Glu | Ser | Met | Ala |
| 145 | | | | | 150 | | | | | 155 | | | | | 160 |
| Ile | Tyr | Lys | Ser | Met | Asp | Tyr | Gly | Arg | Thr | Trp | Val | Pro | Phe | Gln | Phe |
| | | | | 165 | | | | | 170 | | | | | 175 | |
| Tyr | Ser | Thr | Gln | Cys | Arg | Lys | Met | Tyr | Asn | Arg | Pro | His | Arg | Ala | Pro |
| | | | 180 | | | | | 185 | | | | | 190 | | |
| Ile | Thr | Lys | Gln | Asn | Glu | Gln | Glu | Ala | Val | Cys | Thr | Asp | Ser | His | Thr |
| | | 195 | | | | | 200 | | | | | 205 | | | |
| Asp | Met | Arg | Pro | Leu | Ser | Gly | Gly | Leu | Ile | Ala | Phe | Ser | Thr | Leu | Asp |
| | 210 | | | | | 215 | | | | | 220 | | | | |
| Gly | Arg | Pro | Ser | Ala | His | Asp | Phe | Asp | Asn | Ser | Pro | Val | Leu | Gln | Asp |
| 225 | | | | | 230 | | | | | 235 | | | | | 240 |
| Trp | Val | Thr | Ala | Thr | Asp | Ile | Arg | Val | Ala | Phe | Ser | Arg | Leu | His | Thr |
| | | | | 245 | | | | | 250 | | | | | 255 | |

| | | | | | | | | | | | | | | |
|---|---|---|---|---|---|---|---|---|---|---|---|---|---|---|
| Phe | Gly | Asp | Glu 260 | Asn | Glu | Asp | Asp 265 | Ser | Glu | Leu | Ala | Arg 270 | Asp | Ser | Tyr |
| Phe | Tyr | Ala 275 | Val | Ser | Asp | Leu | Gln 280 | Val | Gly | Gly | Arg | Cys 285 | Lys | Cys | Asn |
| Gly | His 290 | Ala | Ala | Arg | Cys | Val 295 | Arg | Asp | Arg | Asp | Asp 300 | Ser | Leu | Val | Cys |
| Asp 305 | Cys | Arg | His | Asn | Thr 310 | Ala | Gly | Pro | Glu | Cys 315 | Asp | Arg | Cys | Lys | Pro 320 |
| Phe | His | Tyr | Asp | Arg 325 | Pro | Trp | Gln | Arg | Ala 330 | Thr | Ala | Arg | Glu | Ala 335 | Asn |
| Glu | Cys | Val | Ala 340 | Cys | Asn | Cys | Asn | Leu 345 | His | Ala | Arg | Arg | Cys 350 | Arg | Phe |
| Asn | Met | Glu 355 | Leu | Tyr | Lys | Leu | Ser 360 | Gly | Arg | Lys | Ser | Gly 365 | Gly | Val | Cys |
| Leu | Asn 370 | Cys | Arg | His | Asn | Thr 375 | Ala | Gly | Arg | His | Cys 380 | His | Tyr | Cys | Lys |
| Glu 385 | Gly | Tyr | Tyr | Arg | Asp 390 | Met | Gly | Lys | Pro | Ile 395 | Thr | His | Arg | Lys | Ala 400 |
| Cys | Lys | Ala | Cys | Asp 405 | Cys | His | Pro | Val | Gly 410 | Ala | Ala | Gly | Lys | Thr 415 | Cys |
| Asn | Gln | Thr | Thr 420 | Gly | Gln | Cys | Pro | Cys 425 | Lys | Asp | Gly | Val | Thr 430 | Gly | Ile |
| Thr | Cys | Asn 435 | Arg | Cys | Ala | Lys | Gly 440 | Tyr | Gln | Gln | Ser | Arg 445 | Ser | Pro | Ile |
| Ala | Pro 450 | Cys | Ile | Lys | Ile | Pro 455 | Val | Ala | Pro | Pro | Thr 460 | Ala | Ala | Ser |
| Ser 465 | Val | Glu | Glu | Pro | Glu 470 | Asp | Cys | Asp | Ser | Tyr 475 | Cys | Lys | Ala | Ser | Lys 480 |
| Gly | Lys | Leu | Lys | Ile 485 | Asn | Met | Lys | Lys | Tyr 490 | Cys | Lys | Lys | Asp | Tyr 495 | Ala |
| Val | Gln | Ile | His 500 | Ile | Leu | Lys | Ala | Asp 505 | Lys | Ala | Gly | Asp | Trp 510 | Trp | Lys |
| Phe | Thr | Val 515 | Asn | Ile | Ile | Ser | Val 520 | Tyr | Lys | Gln | Gly | Thr 525 | Ser | Arg | Ile |
| Arg | Arg 530 | Gly | Asp | Gln | Ser | Leu 535 | Trp | Ile | Arg | Ser | Arg 540 | Asp | Ile | Ala | Cys |
| Lys 545 | Cys | Pro | Lys | Ile | Lys 550 | Pro | Leu | Lys | Lys | Tyr 555 | Leu | Leu | Leu | Gly | Asn 560 |
| Ala | Glu | Asp | Ser | Pro 565 | Asp | Gln | Ser | Gly | Ile 570 | Val | Ala | Asp | Lys | Ser 575 | Ser |
| Leu | Val | Ile | Gln 580 | Trp | Arg | Asp | Thr | Trp 585 | Ala | Arg | Arg | Leu | Arg 590 | Lys | Phe |
| Gln | Gln | Arg 595 | Glu | Lys | Lys | Gly | Lys 600 | Cys | Lys | Lys | Ala | | | | |